United States Patent
Church et al.

(10) Patent No.: US 6,572,871 B1
(45) Date of Patent: Jun. 3, 2003

(54) PAIN TREATMENT METHOD AND APPARATUS USING HEATING WRAP AND ANALGESIC CREAM

(76) Inventors: W. Edward Church, 3810 Gunn Hwy., Tampa, FL (US) 33624; Randall Krafft, 3810 Gunn Hwy., Tampa, FL (US) 33624

( * ) Notice: Subject to any disclaimer, the term of this patent is extended or adjusted under 35 U.S.C. 154(b) by 0 days.

(21) Appl. No.: 09/228,771

(22) Filed: Jan. 6, 1999

(51) Int. Cl.[7] .................. A01N 25/34; A61F 13/00; A61K 9/70; A61L 15/16; A61L 15/00

(52) U.S. Cl. ............... 424/402; 424/443; 424/445; 424/447; 424/449

(58) Field of Search ................ 424/402, 443, 424/445, 447, 449; 514/159, 560; 604/304, 308

(56) References Cited

U.S. PATENT DOCUMENTS

| | | | | |
|---|---|---|---|---|
| 4,736,088 A | * | 4/1988 | Bart | 219/211 |
| 5,013,726 A | * | 5/1991 | Ivy et al. | 514/159 |
| 5,451,747 A | * | 9/1995 | Sullivan et al. | 219/528 |
| 5,603,959 A | * | 2/1997 | Horrobin et al. | 424/490 |
| 5,658,583 A | * | 8/1997 | Zhang et al. | 424/402 |

FOREIGN PATENT DOCUMENTS

| | | | |
|---|---|---|---|
| WO | WO 87/02891 | * | 5/1987 |

OTHER PUBLICATIONS

Taber's Cyclopedic Medical Dictionary (F.A. Davice Company, 1993) p. 91.*
Merriam–Webster's Collegiate Dictionary (Merriam–Webster, Inc 1998) p. 41.*

* cited by examiner

*Primary Examiner*—Thurman K. Page
*Assistant Examiner*—Todd D Ware
(74) *Attorney, Agent, or Firm*—Pedersen & Co., PLLC; Ken J. Pedersen; Barbara S. Pedersen

(57) ABSTRACT

The present invention comprises a heating wrap for placement against an injured/painful area of a person's body and an analgesic cream being placed between the heating wrap and the injured/painful area. The invented cream is formulated specifically for use with a heating wrap to be heat-compatible. The added heat from the heating wrap enhances the permeability of the skin and the tendency of the cream to permeate into the skin. The cream preferably includes an ingredient pharmaceutically categorized as an analgesic agent and an ingredient pharmaceutically categorized as an anti-inflammatory agent. Preferably, the cream does not include ingredients at levels that irritate human skin at the elevated temperatures of the heating wrap, that is, at about 110–140 degrees F. wrap temperatures. The heat wrap may be a pad that includes a flexible sleeve for receiving and surrounding the pad, plus a set of straps for holding the pad or pad/sleeve combination on the body area that is to be treated. Also, the preferred heating wrap includes a thin sheet that will absorb water, which sheet may be dampened with water and inserted between the heating pad and surrounding flexible sleeve, for providing moist heat treatment.

9 Claims, 4 Drawing Sheets

PAIN TREATMENT METHOD AND APPARATUS USING HEATING WRAP AND ANALGESIC CREAM

BACKGROUND OF THE INVENTION

1. Field of the Invention

This invention pertains generally to heating pads and to methods for using heating pads. More specifically, this invention pertains to using a heating pad in conjunction with a heat-activated analgesic cream to provide pain relief.

2. Related Art

For a long time, mankind has used heat to help heal wounds, bruises and discomforts. Heat has been applied to the human body in many ways. Mankind has also used analgesic creams to treat the pain of arthritis, backache, muscle pain, joint pain, abdominal pain, strains and bruises. Analgesic creams also have been applied to the human body in many ways. Conventional analgesic creams include one or more ingredients that relieve pain when topically applied, for example, a salicylate ingredient in the range of 10–60 wt % of the cream.

Still, there has not been to date an effective treatment technique which combines the positive effects of heating pad treatment with the simultaneous use of an analgesic cream. This invention addresses that need for such a treatment.

SUMMARY OF THE INVENTION

The present invention comprises a heating pad for placement against an injured/painful area of a person's body and an analgesic cream being placed between the heating pad and the injured/painful area. Unlike conventional analgesic creams, which are specifically not usable with heating pads or other additional heat applications, the invented cream is formulated specifically to be heat-compatible for use with a heating pad. In fact, the added heat from the heating pad effects)the skin to enhance the permeation of cream into the skin and, thereby, increases the effectiveness of the analgesic cream. The cream preferably does not include ingredients that qualify as irritants to human skin, and, specifically, the cream preferably does not contain any capsaicin or any capsicum-derived ingredients.

Various heating means may be used for covering the affected area that has the invented topically-applied analgesic cream on the skin surface. For example, a heating wrap powered by electricity may be used, such as a commercially-available heating pad. Or, a heating wrap that is heated by an exothermic chemical reaction may be used, based on technology similar to that used in the commercially-available pads for warning a person's cold feet or hands. The preferred heating means is an electrical heating pad that is thermostatically-controlled. The preferred thermostat system is designed to control the pad surface within a relatively narrow temperature range that has been determined to result in a temperature at the skin surface, called a "contact" temperature, that is believed to be optimum for blood circulation, cream permeation into the skin, and pain relief.

The heating system preferably includes a flexible cloth sleeve for receiving and surrounding the pad, plus a set of straps for holding the pad, sleeve, or pad and sleeve combination against the body area that is to be treated. Preferably, the straps are elastic or otherwise adjustable, to let the user adjust the amount of tension on the straps and therefore the pressure of the pad/sleeve against the skin. Preferably, the straps are of two different lengths and may be connected end-to-end to make a single, composite long strap. Also, the preferred heating system also includes a thin foam sheet, which sheet may be dampened with water and inserted between the heating pad and surrounding flexible sleeve. This way, the option of moist heat treatment may be made available. If dry heat is preferred, the damp foam insert is not used.

DESCRIPTION OF THE PREFERRED EMBODIMENTS

Figure 1:
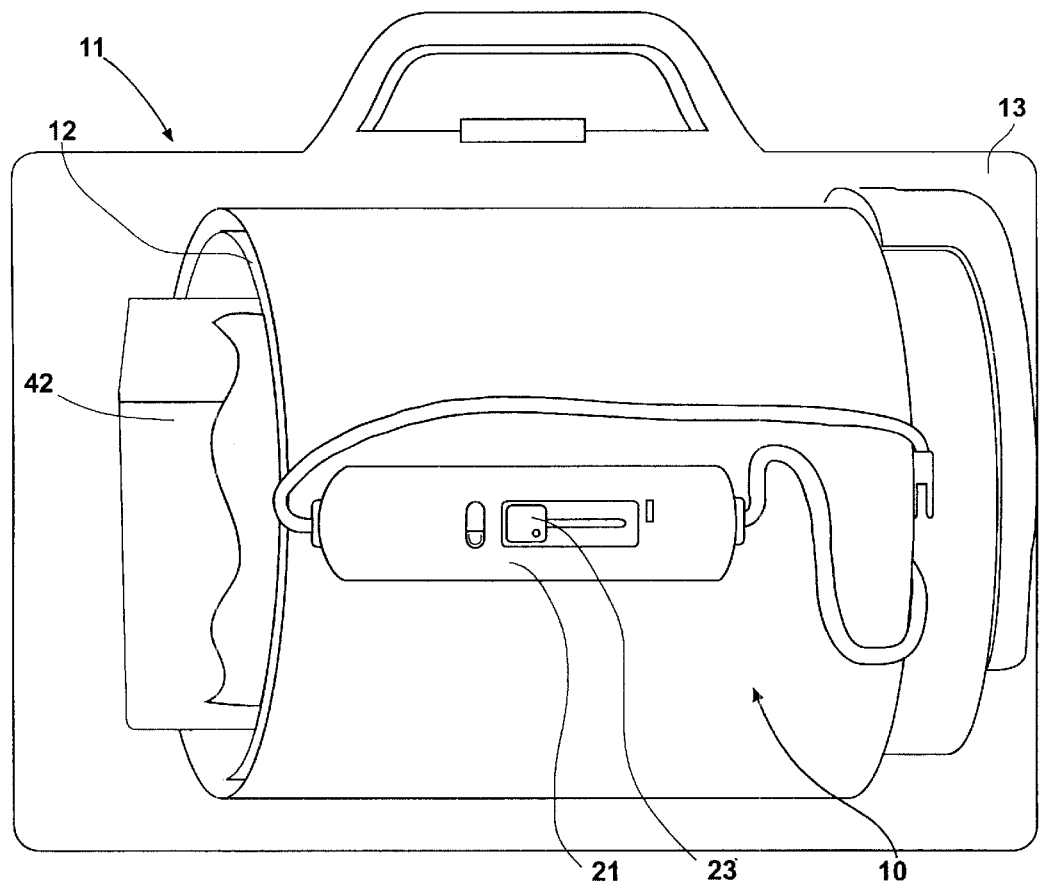
FIG. 1 is a side view of one embodiment of the invention, in a kit including an embodiment of the invented heating pad and an embodiment of the invented treatment cream.
Figure 2:
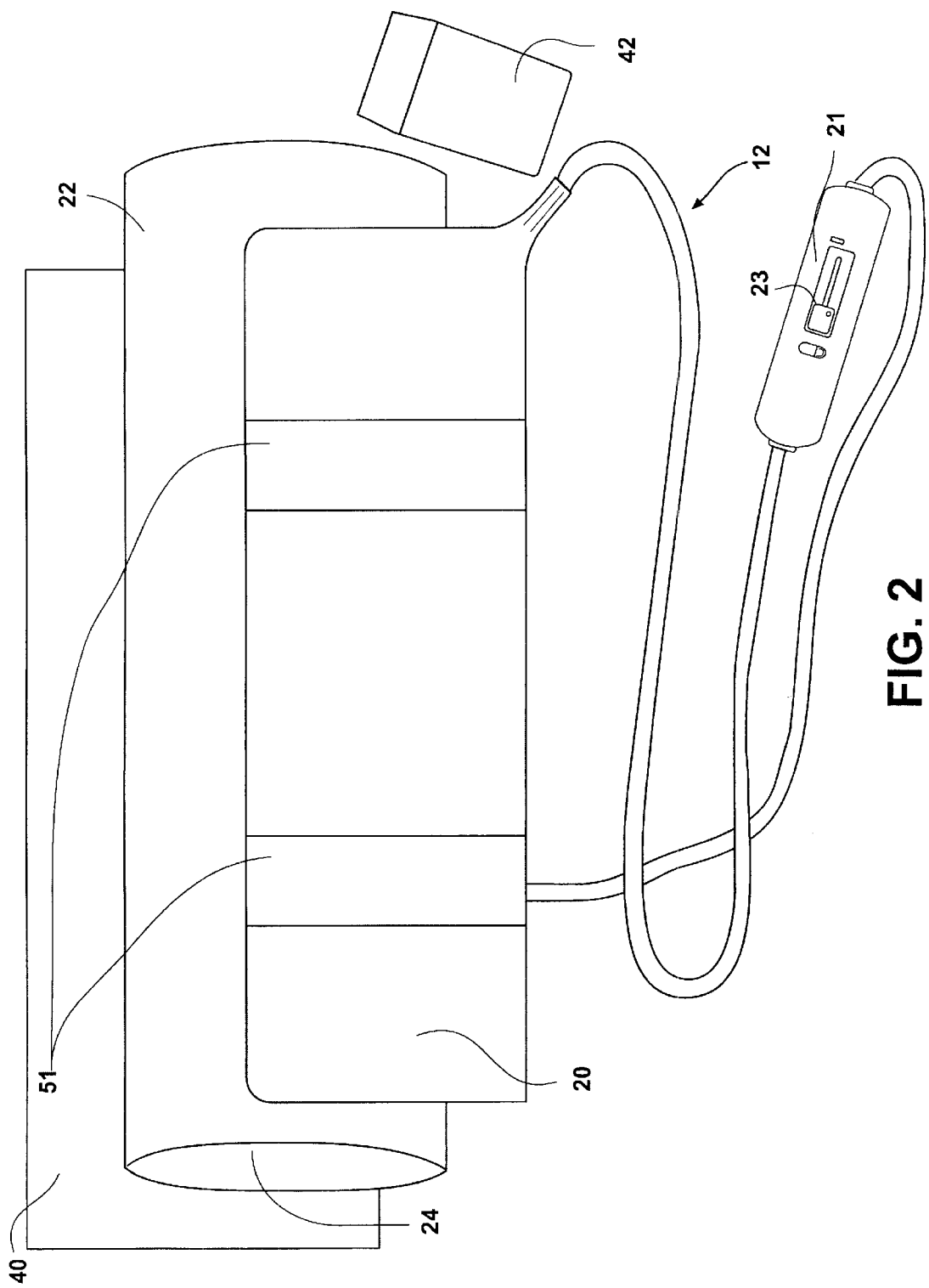
FIG. 2 is a side, perspective view of the heating pad, sleeve, foam sheet, and cream of the embodiment depicted in FIG. 1.
Figure 3:
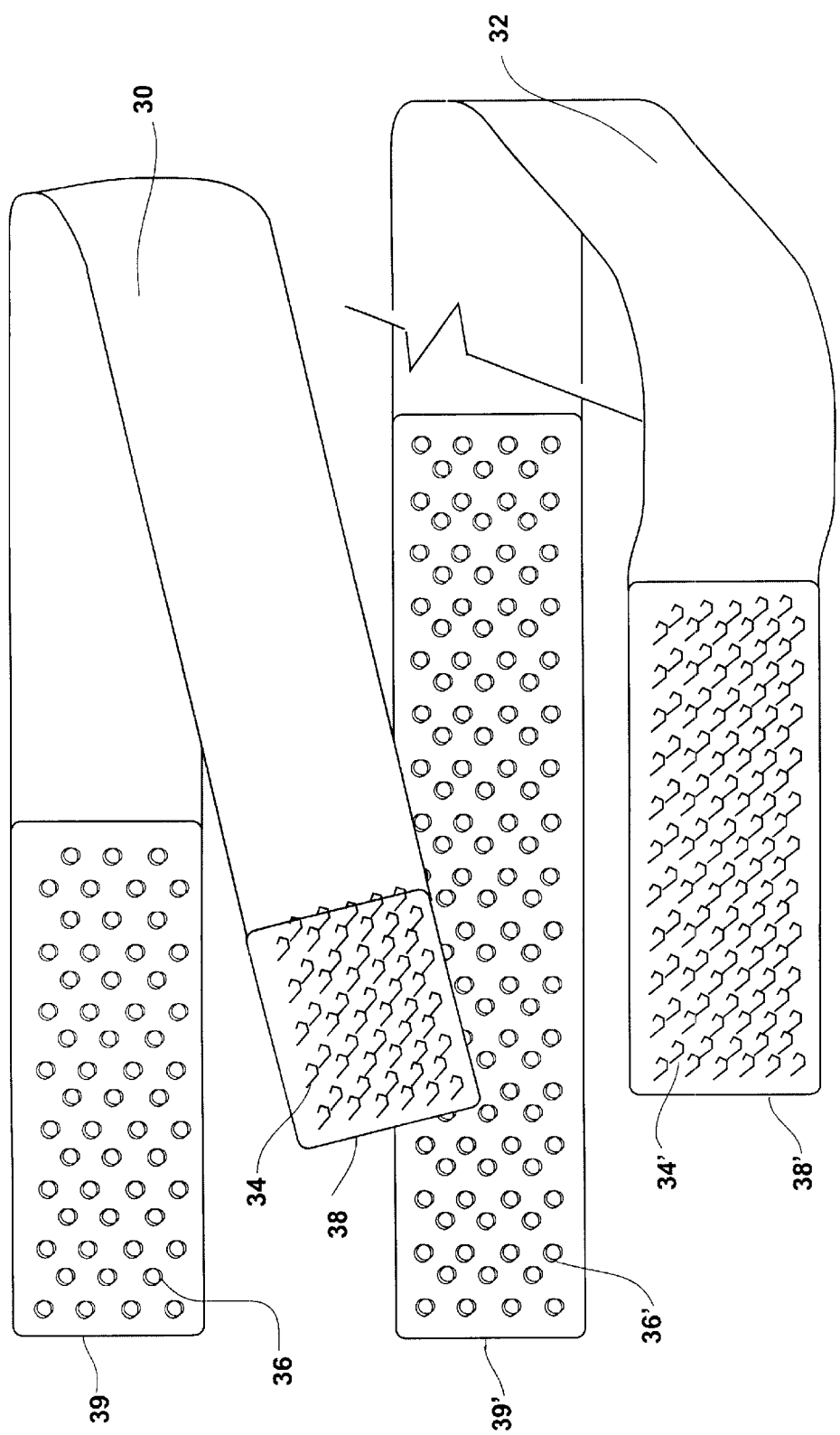
FIG. 3 is a side, perspective view of the heating pad straps of the embodiment depicted in FIG. 1.
Figure 4:
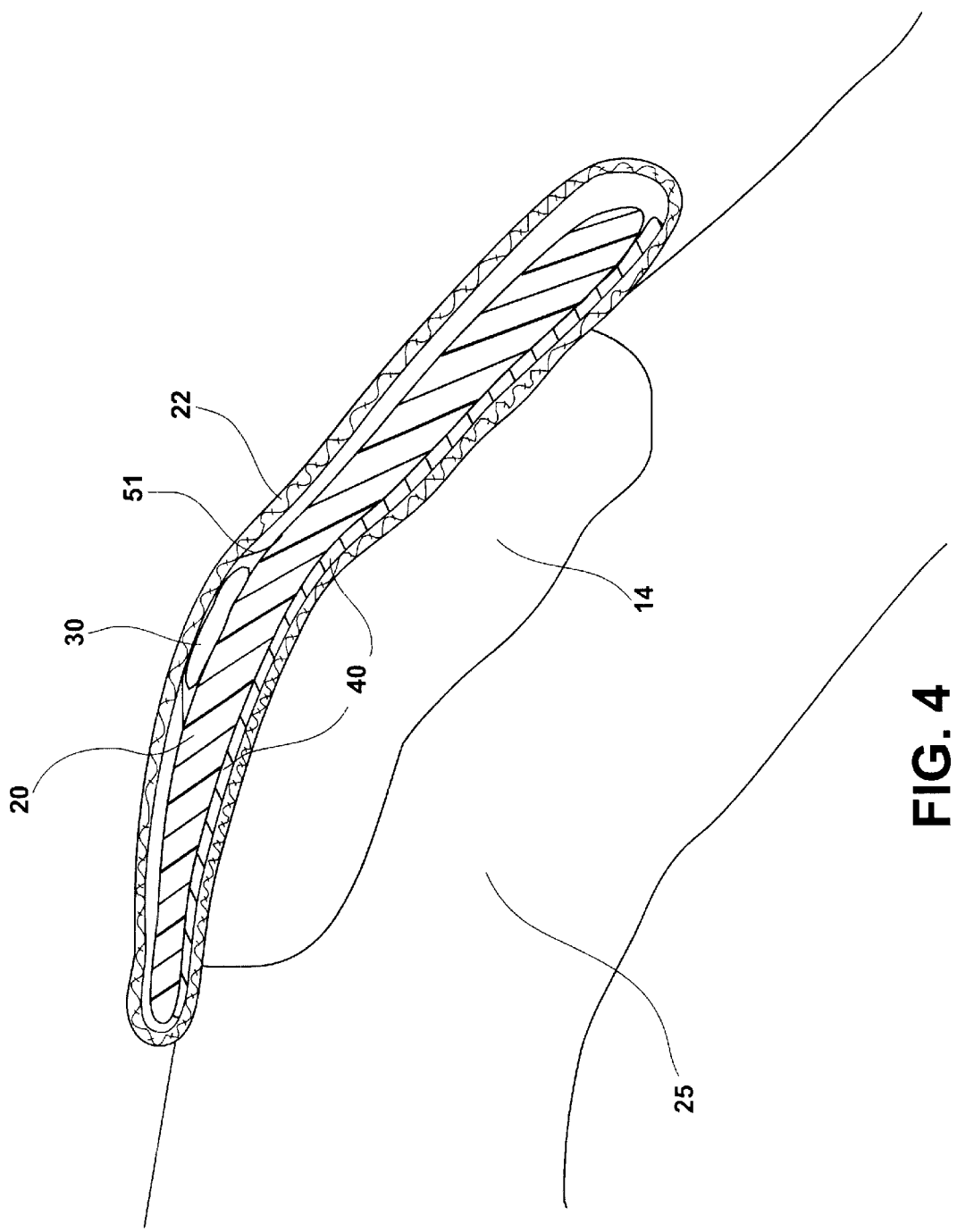
FIG. 4 is a side view of the embodiment of FIG. 1 in use on a body area in need of treatment, with the heating pad, foam layer, and sleeve shown in cross-section.

Referring to the Figures, there is shown one, but not the only, embodiment of the invented deep-heating treatment system for treatment of a painful body area. FIG. 1 shows the invented system in a kit 11 in a plastic case 13 with a handle, and FIGS. 2 and 3 show the pieces-parts of the invented system. FIG. 4 schematically illustrates the simultaneous use of the invented heating pad and analgesic cream combination.

The invented system 10 includes a heating pad 12 and analgesic cream 14 (preferably in cream container 42), the cream 14 being formulated to be compatible and effective with the application of heat that raises the contact temperature (measured by placement of a sensor against the skin surface) to be above about 98 degrees F. The invented cream 14 includes an analgesic ingredient, preferably in or slightly below the lower end of standard analgesic concentrations, that is, in the range of 5–15 wt % (preferably 10 wt-%) compared to the standard analgesic concentration range of 10–60 wt %. Methyl salicylate is especially-preferred because of its analgesic but low-odor characteristics, but menthol or other analgesics may be used. The preferred analgesic cream 14 also includes an anti-inflammatory ingredient, such as linoleic ester, aloe vera gel, garden balsam leaf extract, willow extract, and/or horsechestnut extract. Preferably, the cream 14 has very low levels or no capsaicin or other capsicum-derived ingredients or other ingredients that irritate the skin at the elevated temperatures used in this invention. By "very low levels" is meant that capsaicin is preferably present at less than 0.025 wt % and, more preferably, less than 50 wt-ppm.

The heating pad 12 includes a heating wrap 20, which wrap 20 may be of conventional heating pad construction, plus a temperature control system 21 with control settings/programming designed to maintain a skin surface temperature preferably in the range of about 98–125 degrees F., or in the especially-preferred range of about 103–118 degrees F. To do this, the electrical current is turned on/off, that is, "pulsed" through the wrap heating wires, to result in a thermocouple temperature in the wrap's interior in the range of about 115–135° F. and a wrap surface temperature in the range of about 110–140 degrees F. The thermostat system, therefore, is designed to work off of set points that are selected by a button or switch 23, to allow the user some choice of temperature level: Setting One preferably corresponds to about a 115° F. wrap thermocouple temperature and a 103–105° F. skin temperature, Setting Two preferably corresponds to about a 125° F. thermocouple temperature and a 106–109° F. skin temperature; and Setting Three corresponds to about a 135° F. thermocouple temperature and a 110–113° F. skin temperature. This addition of heat into the skin of the cream-treated body area 25 over time causes a deep-heating of the body tissue, without overheating the skin, which increases blood flow and increases the skin's permeability to the cream, and consequently increased deep-penetration of the herbal, analgesic, anti-inflammatory, and other ingredients of the cream. The heating pad system may include a sleeve 22 with an interior space 24 for receiving the heating pad 10 and the portions of the strap(s)(30, 32) that extend through the loops 52 on a side of the wrap 20, or, optionally that extend through loops on the sleeve or that connect in other ways to the wrap. The sleeve 22 is preferably a flexible, soft cloth rather than a plastic surface, for contacting the body area 25 with associated comfort, washability, and aesthetics. The sleeve preferably covers substantially all of both sides of the pad and is easily removable, for example, comprising two open ends with no straps, snaps, or other attachments to the wrap 20.

The system 10 may include one or more straps 30, 32 for holding the wrap 20 and sleeve 22 in place against the body area 25. Preferably, two straps 30, 32 are supplied, each of which has cooperating hook and loop patches 34, 34', 36 and 36' on opposing ends 38, 38', 39 and 39'. Preferably, the first strap 30 has a length (about 15–18 inches) about half the length (28–36 inches) of the second strap 32. The first strap's patches 34, 36 have a length of about 2 and 5 inches, respectively, which is about half the length (4 and 8 inches) of the second strap's patches 34', 36'. This combination of short and long straps and patches results in increased adaptability for securing the pad 20/sleeve 22 to the body area. For example, the short strap may be for securement to a knee or an elbow, and the long strap may be for securement to a shoulder or around the waist. Connecting the two straps 30, 32 together end-to-end creates a single, extra-long strap that may be used for special circumstances, such as securement around a large-sized patient's waist to treat the sides or back of the patient.

An optional foam layer 40 or other water-holding sheet may be used for providing moist heat treatment. The foam layer 40 is dampened with water and inserted between the heating wrap 20 and surrounding flexible sleeve 22. Then, the heat from wrap 20 conducts through the foam layer 40, through the sleeve 22 to the skin, while warm moisture from the foam layer 40 also permeates through the sleeve to the skin. The foam layer 40 may preferably be about the size of one side of the heating wrap 20, and is preferably about 1/8" thick open-celled, polymer foam material.

The invented cream 14 in cream container 42 is an analgesic cream, which cream includes an analgesic ingredient and one or more an anti-inflammatory ingredients, as discussed above, herbal and other natural components and extracts, as well as emollients and skin conditioners. A preferred list of ingredients for cream 14 is: methyl salicylate at about 10 wt-%, plus:

aloe vera gel;
linoleic esters;
garden balsam leaf extract;
coconut waxes;
allantoin;
panthenol;
hyaluronic acid;
jasmine essence;
willow extract;
echinacea;
horsechestnut extract;
basabalol; and
sodium benzoate.

Aloe vera gel is a major component of the preferred cream and may be considered an anti-inflammatory ingredient. Also, the garden balsam leaf extract, willow extract, and horsechestnut extract are considered anti-inflammatory ingredients, as well as the linoleic ester. An especially preferred linoleic ester is derived from a zwitterionic (dipolar ion) fatty acid. The preferred analgesic ingredient is methyl salicylate.

The aloe vera gel is preferably about 50 wt-% of the cream. The linoleic ester concentration may be, for example, from about 1 to 10 wt-%. The preferred analgesic ingredient, methyl salicylate, is included in the cream at about 10 wt %. The other ingredients may be included in various amounts from traces to about 5 wt-%, or at typical ranges for conventional topical ointments and creams.

Many of these ingredients may be said to be "heat-activated," as they become more fluid and more aromatic with temperature, and, therefore, more likely to penetrate into the skin, which itself is more permeable due to the heat. The overall result is more blood flow, deeper permeation of the cream, soothing and pain-relief of the tissue, and encouragement of healing.

Preferably, what is purposely kept out of the analgesic cream, is any component that significantly irritates or burns the skin at the elevated skin temperatures of this invention. Specifically, capsaicin or other capsicum-derived components are eliminated from the formulation or, at the most, included at low levels, that is, less than 0.025 wt-% and more preferably less than 50 ppm. Capsaicin is included in conventional analgesic creams, at concentrations from 0.025 wt-% up to about 0.25 wt-%, as a self-heating "exothermic" component that gives the "deep-heating" feature advertised by some commercially-popular creams. The preferred embodiments of the invention exclude capsaicin, to prevent irritation and burning of the skin, especially at the temperatures of the methods of the invention. The inventors believe that their invented cream, without capsaicin, creates a non-irritating analgesic cream which is enhanced by heat from the pad 20, but that does not exothermically overheat or irritate the skin or body tissue. Thus, the invented cream plus heating from the thermostatically-controlled heating pad, creates a novel deep-heating, but controlled and non-burning and nonirritating, environment at the skin.

In use, the following preferred steps are used:

1. The heating pad is plugged into a 110 volt electrical outlet, with the control set at the lowest setting, Setting 1.

2. Apply a large, pearl-sized drop of the cream onto the affected area, and gently rub the cream onto the skin.

3. Insert one of the elastic straps 30, 32 longitudinally through the two plastic loops 51 on the wrap 20. Use the shorter elastic strap when positioning the pad on arms and legs. Use the longer elastic strap for the waist area. Combine the two straps when an extra-long strap is needed.

4. Insert the heating wrap, with its connected straps, through the cloth sleeve, so that the strap ends extend out from the sleeve.

5. Place the heating wrap over the affected body area and secure firmly yet comfortably with the elastic straps by wrapping the strap ends around the body part to be treated and connecting the hook and loop patches together.

6. Apply the cream and heating wrap for about 15 to 30 minutes each time an area is treated. If needed, reapply the heat wrap, preferably after waiting 45 to 60 minutes.

Although this invention has been described above with reference to particular means, materials and embodiments, it is to be understood that the invention is not limited to these disclosed particulars, but extends instead to all equivalents within the scope of the following claims.

We claim:

1. An analgesic treatment apparatus comprising the combination of:

an analgesic cream for application on an area of skin of a person, the analgesic cream comprising aloe vera gel, 5–15 wt-% salicylate compound, and 1–10 wt-% zwitterionic-fatty-acid linoleic ester;

a heating device with a surface for placement against said area of skin after application of said analgesic cream, wherein the heating device comprises a temperature control system adapted so that the heating device heats said area of skin to, and maintains said area of skin in, a temperature in the range of 103–118° F. by controlling the surface to have a surface temperature in the range of 110–140° F. by controlling the surface to have a surface temperature in the range of 110–140° F. so that said area of skin becomes more permeable due to said heating to, and maintaining in, the temperature range of 103–118° F.;

wherein said analgesic cream becomes more fluid when said area of skin is heated and maintained to the temperature in the range of 103–118° F.;

wherein said combination of analgesic cream and heating device that heats and maintains said area of skin in the temperature in the range of 103–118° F. does not cause burns on said area of skin.

2. The analgesic treatment apparatus of claim 1, wherein the salicylate compound is methyl salicylate.

3. The analgesic treatment apparatus of claim 1, wherein the analgesic cream further comprises an anti-inflammatory ingredient in the range of 1–50 wt % of the analgesic cream, wherein the anti-inflammatory ingredient is selected from the group consisting of garden balsam leaf extract, willow extract, and horse chestnut.

4. The analgesic treatment apparatus of claim 1, wherein the cream contains less than 50 wt-ppm capsaicin.

5. The analgesic treatment apparatus of claim 1, wherein the heating device comprises a cloth sleeve around the heating means and placing the cloth sleeve against said area of skin to which the analgesic cretin is applied.

6. The analgesic treatment apparatus of claim 5, further comprising a water-holding sheet between the heating device and the cloth sleeve to provide a moist environment near said area of skin.

7. An analgesic treatment method comprising:

applying an analgesic cream to an area of skin of a person; and applying a heating device against said area of skin after application of said analgesic cream, and thermostatically-controlling said heating device so that the heating device heats said area of skin to, and maintains said area of skin in, a temperature range of 103–118° F. by controlling the surface to have a surface temperature in the range of 110–140° F. by controlling the surface to have a surface temperature in the range of 110–140° F. so that said area of skin becomes more permeable due to said heating to, and maintaining in, the temperature range of 103–118° F.;

wherein said analgesic cream comprises aloe vera gel, 1–10 wt-% zwitterionic-fatty-acid linoleic ester, and 5–15 wt % of a salicylate compound; and wherein applying said analgesic cream and heating and maintaining said area of skin to 103–118° F does not cause burns on said area of skin.

8. An analgesic treatment method of claim 7, wherein the salicylate compound is methyl salicylate.

9. An analgesic treatment method of claim 7, wherein the analgesic cream further comprises an anti-inflammatory ingredient in the range of 1–50 wt % of the analgesic cream, wherein the anti-inflammatory ingredient is selected from the group consisting of garden balsam leaf extract, willow extract, and horse chestnut.

* * * * *

UNITED STATES PATENT AND TRADEMARK OFFICE
CERTIFICATE OF CORRECTION

PATENT NO. : 6,572,871 B1
APPLICATION NO. : 09/228771
DATED : June 3, 2003
INVENTOR(S) : Church et al.

Page 1 of 1

It is certified that error appears in the above-identified patent and that said Letters Patent is hereby corrected as shown below:

On Title page (item 76)
Inventors: W. Edward Church
Randall Krafft
Peter T. Pugliese
Peter M. Pugliese Signed and Sealed this Twenty-ninth Day of August, 2006

JON W. DUDAS
*Director of the United States Patent and Trademark Office*